United States Patent [19]
Jolly

[11] Patent Number: 5,999,859
[45] Date of Patent: Dec. 7, 1999

[54] APPARATUS AND METHOD FOR PERIMODIOLAR COCHLEAR IMPLANT WITH RETRO-POSITIONING

[75] Inventor: Claude Jolly, Zifres/Axams, Austria

[73] Assignee: Med-El- Elektromedizinische Gerate G.m.b.H., Innsbruck, Austria

[21] Appl. No.: 09/037,893

[22] Filed: Mar. 10, 1998

Related U.S. Application Data

[60] Provisional application No. 60/040,499, Mar. 10, 1997, and provisional application No. 60/071,375, Jan. 15, 1998.

[51] Int. Cl.⁶ ........................................................ A61N 1/05
[52] U.S. Cl. .............................................................. 607/137
[58] Field of Search ............................................ 607/137

[56] References Cited

U.S. PATENT DOCUMENTS

| | | | |
|---|---|---|---|
| 4,898,183 | 2/1990 | Kuzma | 607/137 |
| 5,370,679 | 12/1994 | Atlee, III | 607/124 |
| 5,545,219 | 8/1996 | Kuzma | 607/137 |
| 5,645,585 | 7/1997 | Kuzma | 607/137 |
| 5,653,742 | 8/1997 | Parker et al. | 607/137 |

FOREIGN PATENT DOCUMENTS

| | | |
|---|---|---|
| 0 002 068 | 5/1979 | European Pat. Off. . |
| 2 465 474 | 3/1981 | France . |
| 42 00 030 | 7/1993 | Germany . |
| WO 94 00088 | 1/1994 | WIPO . |
| WO 96 31087 | 10/1996 | WIPO . |

*Primary Examiner*—William E. Kamm
*Attorney, Agent, or Firm*—Bromberg & Sunstein LLP

[57] ABSTRACT

An implantable cochlear electrode array includes an electrode carrier, a groove within the electrode carrier, and a flexible element located in the groove. After the electrode array is implanted, the flexible element may be held in place while the electrode carrier may be partially withdrawn so that the electrode carrier pulls away from the flexible element which emerges from the groove through the surface of the electrode carrier, except where the electrode carrier and the flexible element are attached, so that the electrode carrier wraps around an inner scala tympani wall. A portion of the apical end of the electrode carrier may extend beyond the ends of the groove and the flexible element so that the apical end of the electrode carrier does not wrap around the inner scala tympani wall when the electrode carrier is partially withdrawn after insertion in the cochlea. The electrode carrier may include a perimodiolar section to be positioned next to an inner scala tympani wall of the cochlea, and an outer wall section to be positioned next to an outer scala tympani wall of the cochlea. The perimodiolar section may be shorter than the outer wall section to accommodate the real length difference between the inner and outer walls of the scala tympani of a cochlea. Preferred embodiments are also directed to a method of fabricating a such a cochlear electrode array by negative casting, and to a method of implanting such a cochlear electrode array.

38 Claims, 9 Drawing Sheets

APPARATUS AND METHOD FOR PERIMODIOLAR COCHLEAR IMPLANT WITH RETRO-POSITIONING

This application claims the benefit of the earlier filing date of U.S. provisional patent application Ser. No. 60/040,499, filed Mar. 10, 1997, and of U.S. provisional patent application Ser. No. 60/071,375, filed Jan. 15, 1998. These applications are incorporated herein by reference.

TECHNICAL FIELD

The present invention relates to the structure, method of use and method of manufacture of an implanted hearing prosthesis.

BACKGROUND ART

Sounds are transmitted through the outer ear to the eardrum which moves the bones of the middle ear and excites the cochlea. The cochlea is a long narrow duct wound spirally about its axis for approximately two and a half turns. The fluid filled cochlea transmits mechanical sound waves in response to received sounds and in cooperation with the cochlear duct, functions as a transducer to generate electric impulses which are transmitted to the cochlear nerves and thence to the brain.

Profoundly deaf patients have lost the ability to transduce the outer mechanical sound wave into meaningful action potentials along the neural substrate of the cochlea. In persons with total sensorineural hearing loss, therefore, the cochlea does not respond to sound waves to generate electrical signals for transmission to the cochlear nerves. An auditory prosthesis for the deaf requires a suitable stimulation electrode capable of stimulating the auditory nerves. A cochlear implant is a neural prosthesis designed to permanently restore the sensation of sound in profoundly and severely deaf patients, including children.

The interface between the prosthesis and the auditory nerve consists of an electrode carrier inserted into the fluid filled scala tympani region of the cochlea. The scala tympani fluid is highly conductive to electrical current. The anatomy of the scala tympani is that of an upright spiraling cone with an inner wall and an outer wall. The center of the spiral is called the modiolar. The modiolar is where the spiral ganglion cells reside. Cochlear prostheses attempt to stimulate the spiral ganglion cells directly with small currents delivered by a multitude of electrodes regularly distributed along the carrier. The stimulating current is synchronized with the environmental sound via complex input output functions and digital signal processing.

The distance between the excitable spiral ganglion cells and their axons, and the electrode carrier is relatively large, up to 2 mm at the basal end of the cochlea. This distance becomes significant as it causes the threshold and maximum currents responsible for the stimulation to be relatively high. Furthermore, with increasing distance, the potential field generated by adjacent electrodes may stimulate an overlapping population of nerve cells, particularly at higher currents. The spatial selectivity of each electrode is reduced. The dynamic range is also lower. The power consumption of the implanted prosthesis is higher.

Fundamental features of a cochlear implant electrode array carrier must include attributes that allow the carrier to be easily implantable, explantable, reimplantable, and biocompatible. In addition, as very delicate tissues line the scala tympani, the insertion process must prove to be as atraumatic as possible. Finally, a last requisite for a perimodiolar electrode involves the device's ability to hug the modiolus whether the array is fully inserted or not despite the unique geometry of the individuals inner ear canal.

Several methods have been proposed to attempt a displacement or an initial positioning of the cochlear implants proximal to the auditory nerve cells. One manufacturer has routinely implanted a space filling, pre-curved electrode introduced with an insertion tool has been routinely implanted by one manufacturer. Unfortunately, the results of this placement have failed to provide a viable option as the electrode, positioned somewhat between the inner and outer wall of the scala tympani, does not establish adequate contact. Theoretical or experimental devices have been proposed based on 1) a bilaminar array with half of the carrier made of a material which can absorb liquid and increases in length (differential expansion may cause the array to curve in an unpredictable manner), 2) an array with an external and parallel polymer forward positioning, 3) an array with a shape memory nitinol core, 4) a preshaped array made straight with bioresorbable material, and 5) an array with active positioning through the passage of current into a nitinol wire. In vitro and in vivo data concerning the placement of the electrode array in such proposed devices is sketchy or absent. In some cases, the insertion and displacement trauma is estimated unacceptable.

The arduous task of displacing a non-space-filling electrode array from the lateral to medial wall of the scala tympani is compounded by the fact that the inner and outer wall of the scala tympani are respectively 40 and 18 mm long. If the array is fully inserted along the outer wall (about 31 mm for a 0.5 mm diameter electrode), then the process of the array hugging the modiolus, is not a simple radial translation from the lateral wall to the medial wall. Movement of the array from the outer wall to the inner wall principally involves a longitudinal displacement of all points on the array in the axial direction of the scala tympani, and from the apical to basal end. A significant length of the electrode array has to be forced out of the scala tympani. If the array is partially inserted along the outer wall, then the process of the array hugging the modiolus may be either a forward or backward displacement of the array. In the case of a forward displacement, because of the spiraling shape of the cochlea, the necessary longitudinal displacement of points on the array to go from the outer wall to the inner wall increases with distance down the scala tympani.

For example, a point located against the lateral wall 12 mm into the scala tympani has to travel up to a point radially facing the 23 mm outer wall mark to embrace the inner wall of the cochlea. The amount of forward displacement increases linearly from base to apex. Furthermore, points located on the first turn past the 12 mm mark on the outer wall, have to move around the narrowing corner to the second turn of the cochlea to hug the inner wall.

SUMMARY OF THE INVENTION

A preferred embodiment of the present invention is directed towards an implantable cochlear electrode array. In such an embodiment, the array has an electrode carrier having a outer end and an inner end, to electrically stimulate a scala tympani wall of a cochlea in which the carrier is implanted; a groove within the electrode carrier extending from the outer end of the electrode carrier at least part way towards the inner end wherein at least a portion of the groove penetrates the surface of the electrode carrier; and a flexible element located in the groove and attached to the electrode carrier towards the inner end; wherein the carrier and the flexible element are arranged with respect to each other so that, after the electrode array is inserted in a cochlea, movement of the carrier with respect to the flexible element, towards the outer end, causes the electrode carrier to wrap around an inner scala tympani wall. In a further embodiment, the carrier and the flexible element are arranged with respect to each other so that, after the electrode array is inserted in a cochlea, movement of the carrier with respect to the flexible element, towards the outer end, pulls the electrode carrier away from the flexible element which emerges from the groove through the surface of the electrode carrier, except where the electrode carrier and the flexible element are attached, so that the electrode carrier wraps around an inner scala tympani wall.

In related embodiments, the groove may have a fixed or variable cross-sectional shape. The groove cross-sectional shape may be, for example, circular, rectangular, or u-shaped. In an embodiment, the groove may be substantially parallel to a long axis of the electrode carrier, or it may significantly deviate from a long axis of the electrode carrier. In a further embodiment, the groove may have an inner notch located near the inner end to maintain the inner end of the flexible member and an adjacent portion of the electrode carrier together. The flexible element, in an embodiment, may be a wire made of biocompatible material, such as nitinol, and may further have a surface coating to modify its surface characteristics or its dielectric characteristics. Alternatively, the flexible element may be a flexible polymeric rod.

A preferred embodiment may have a portion of the inner end of the electrode array extending beyond the inner ends of the groove and the flexible element so that the inner end of the electrode array does not wrap around the inner scala tympani wall when the electrode carrier is partially withdrawn after insertion in the cochlea. In addition, there may be a bridge portion of the electrode carrier located near the outer end of the electrode carrier which closes over the surface penetration of the groove to form a closed tunnel around the flexible element and to prevent the flexible element from lifting out of the groove at the bridge. A further embodiment may include at least one outer notch near the outer end of the electrode carrier to securely hold the outer end of the flexible member after the electrode array has been implanted in the cochlea.

Another preferred embodiment is directed to an implantable cochlear electrode array. Such an embodiment has an electrode carrier having a outer end and an inner end, to electrically stimulate a scala tympani wall of a cochlea in which the carrier is implanted. The electrode carrier further has a perimodiolar section to be positioned next to an inner scala tympani wall of the cochlea, and an outer wall section to be positioned next to an outer scala tympani wall of the cochlea. The perimodiolar section may be shorter than the outer wall section to accommodate the real length difference between the inner and outer walls of the scala tympani of a cochlea. The implantable array, in this embodiment, also has a groove within the electrode carrier, in either the perimodiolar section or in the outer wall section, extending from the outer end of the electrode carrier at least part way towards the inner end wherein at least a portion of the groove penetrates the surface of the electrode carrier, and a flexible element located in the groove and attached to the electrode carrier towards the inner end. In this embodiment, the carrier and the flexible element are arranged with respect to each other so that, after the electrode array is inserted in a cochlea, movement of the carrier with respect to the flexible element, towards the outer end, causes the perimodiolar section of the electrode carrier to wrap around an inner scala tympani wall. In a further embodiment, the carrier and the flexible element are arranged with respect to each other so that, after the electrode array is inserted in a cochlea, movement of the carrier with respect to the flexible element, towards the outer end, pulls the perimodiolar section of the electrode carrier away from the flexible element which emerges from the groove through the surface of the electrode carrier, except where the electrode carrier and the flexible element are attached, so that the perimodiolar section of the electrode carrier wraps around an inner scala tympani wall.

A preferred embodiment of fabricating a cochlear electrode array uses negative casting. In this embodiment, the method includes forming an injection mold for an electrode carrier in a desired shape, attaching a groove molding wire to one edge of the mold, injecting material, for example silicone, into the mold to form the electrode carrier, and pulling the groove molding wire out of the electrode carrier. In a related embodiment, before the step of pulling the groove molding wire out of the electrode carrier the method may further include cutting a slit along the length of the electrode carrier from an outer surface of the electrode carrier to the groove molding wire.

A preferred embodiment of implanting a cochlear electrode includes inserting the electrode array into a fluid filled cochlea so that the electrode array conforms to an outer scala tympani wall of the cochlea, and positioning the electrode array to displace at least a portion of the electrode array from the outer scala tympani wall toward an inner scala tympani wall so that any undisplaced portion of the electrode array remains against the outer scala tympani wall. The electrode array may be fully or partially inserted into the fluid filled cochlea. In a further embodiment, the step of positioning includes holding in place a flexible element attached within the electrode array towards the inner end of the electrode array, and partially withdrawing the electrode array so that the electrode array separates from the flexible member and pulls away from the outer scala tympani wall of the cochlea towards an inner scala tympani wall of the cochlea.

BRIEF DESCRIPTION OF THE DRAWINGS

The present invention will be more readily understood by reference to the following detailed description taken with the accompanying drawings, in which.

DETAILED DESCRIPTION OF SPECIFIC EMBODIMENTS

A preferred embodiment of the present direction is directed to a straight multi-electrode cochlear prosthesis with an outer (or basal) end and an inner (or apical) end which is designed to be inserted into the upright, conical and spiraling shape of the cochlea. During surgical insertion, the electrode array conforms to the outer wall of the fluid filled scala tympani. The scala tympani is the natural canal into which a cochlear prosthesis is inserted by a surgeon.

A preferred embodiment provides an electrode array designed to displace the whole electrode array, or any portion of it, away from the outer wall of the scala tympani and toward the inner wall. Any undisplaced portion of the electrode array remains against the outer wall. The active displacement of the electrode is performed by a surgeon through a retro-positioning technique. With the retro-positioning technique, the electrode is drawn back after full or partial insertion, except at the apical end where the electrode is held in place within the electrode carrier with a flexible element. Such an element is designed to be flexible enough for ease of insertion yet rigid enough to hold the apical tip of the electrode array stationary throughout the retracting process.

The cochlear prostheses, in a preferred embodiment, is fabricated with an inner tunnel molded near or on the edges of the electrode carrier. The tunnel is cylindrical, rectangular or u-shaped. A slit exposes the inner tunnel to the outer surface of the carrier. The slit tunnel thus forms a microgroove. A wire, rod or ribbon is placed inside the microgroove as the flexible element. The apical end of the flexible element is fixed in a molded silicone notch at the apical end of the carrier. The basal end of the flexible element may slide through a short silicone tunnel molded inside the microgroove.

After insertion of the electrode carrier into the cochlea, the flexible element is held stationary posterior to the cochleostomy by the surgeon. The electrode carrier is then gently retracted. This slight pulling of the electrode carrier out of the cochlea dislocates the inner flexible element from the carrier's microgroove, except at the apex where the flexible element fits into a silicone hollow cavity. The surgeon's continued retracting motion on the electrode carrier causes the array to wrap around the inner wall of the cochlea.

In an alternative embodiment, the electrode carrier is partitioned into two branches. The two confluent branches are initially held together, and after insertion, the confluent branches are separated. In this final state, one branch rests against the outer wall of the scala tympani while the other branch lies against the inner wall.

Figure 1A:
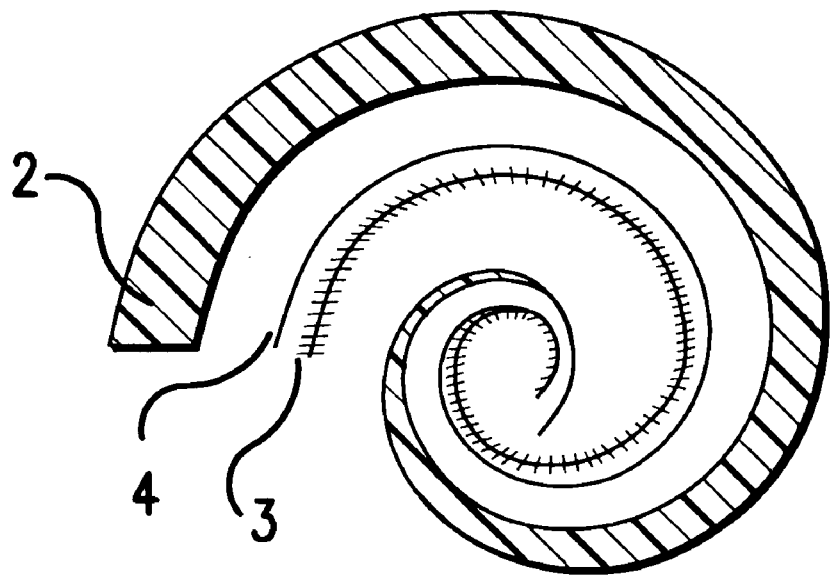
FIGS. 1A and 1B illustrate the position of the electrode array in respectively planar and cross sectional views of the cochlea immediately after insertion.
Figure 1B:
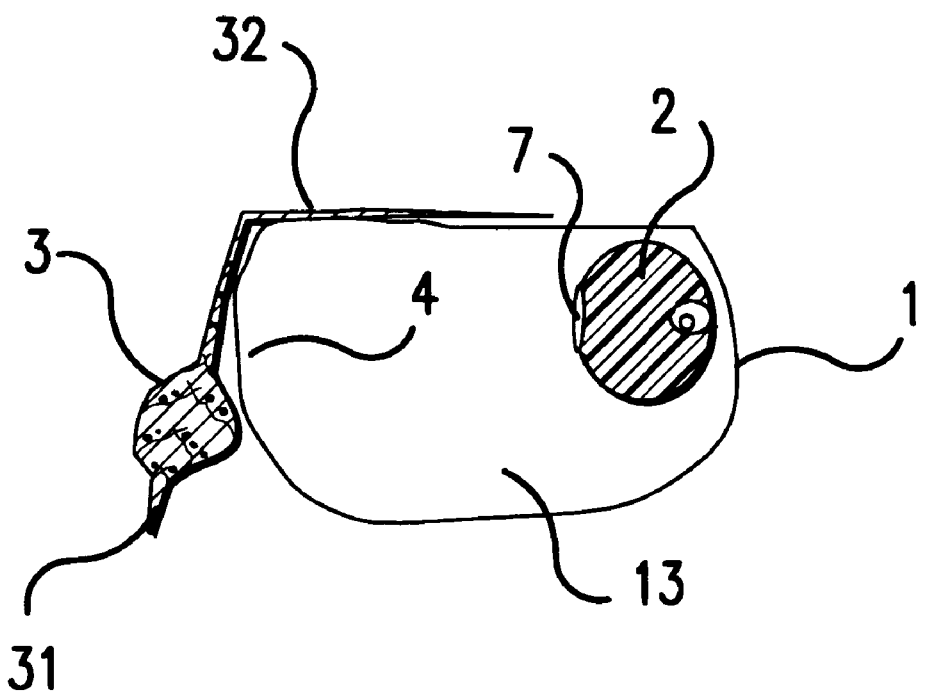
Figure 2A:
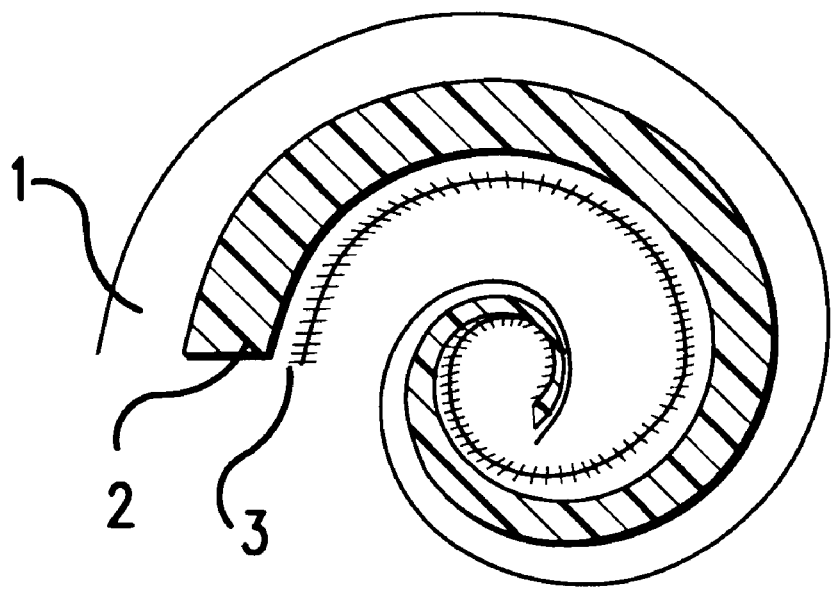
FIGS. 2A and 2B illustrate the position of the electrode array in respectively planar and cross sectional views of the cochlea after retro positioning.
Figure 2B:
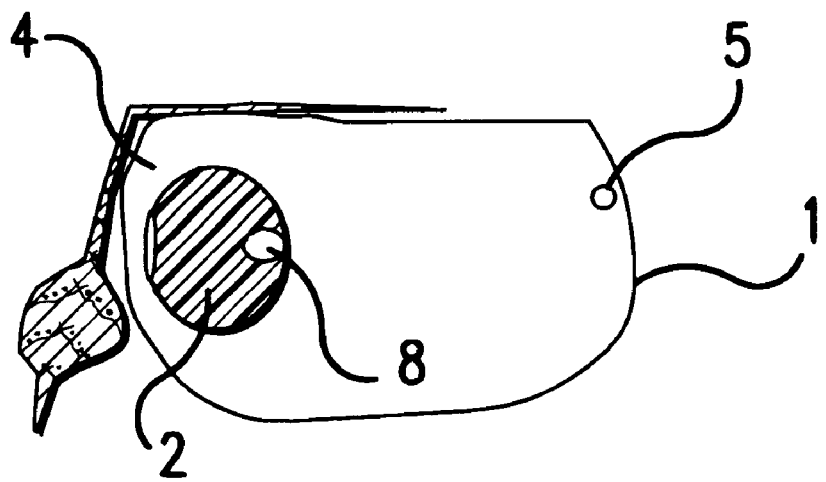

FIGS. 1A–B and 2A–B illustrate a cochlea with an inner wall 4, an outer wall 1, and a spiral ganglion cells population 3. FIG. 1A shows a tapered electrode carrier 2 positioned against the outer wall 1, while FIG. 2A shows the carrier 2 positioned against the inner wall 4. FIGS. 1B and 2B show a cross sectional view of the scala tympani region of a cochlea 13 and the position of electrode carrier 2 before and after retro-positioning of the carrier. As can be observed between FIGS. 1A and 2B, the length of electrode carrier 2 when it lays against the outer wall 1 is longer than when it lays against the inner wall 4.

Figure 3A:
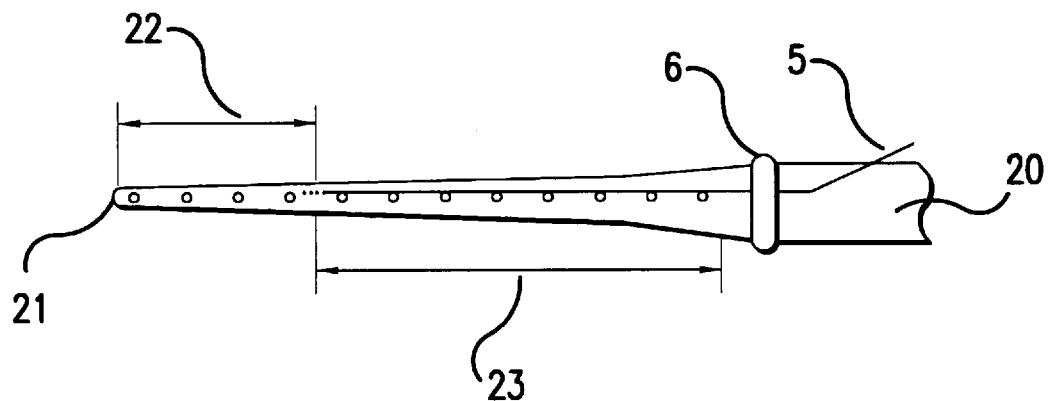
FIGS. 3A and 3B illustrate a perimodiolar electrode array with respectively a short and a long microgroove.
Figure 3B:
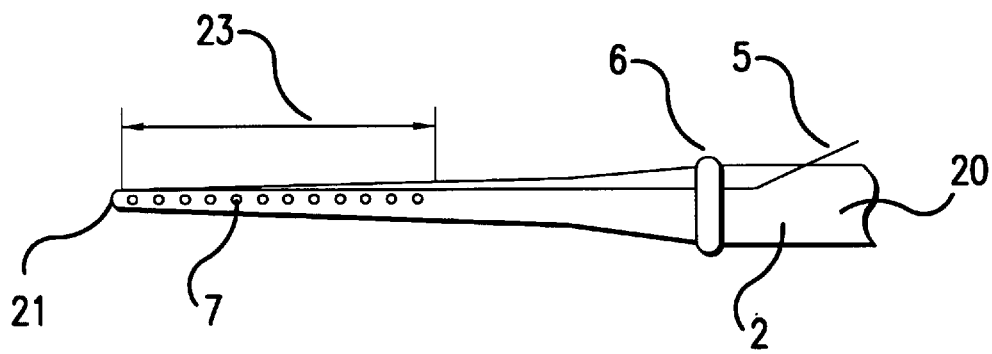

A preferred embodiment provides a reliable way of moving electrode carrier 2 from the outer wall 1 to the inner wall 4 of the scala tympani spiral 13. This is done after insertion of the electrode carrier 2 by retracting the electrode carrier from the cochlea toward the base, in FIG. 3A–B while maintaining in place the electrode carrier apex portion of the carrier 21, where it is fixed by a flexible, yet firm, element 5. Both the electrode carrier 2 and the flexible element 5 have an apical end 20 and a basal end 21. The flexible element 5 may be shorter than electrode carrier 2, as shown in FIG. 3A, or extend to the apical end 21 of the electrode carrier 2, as shown in FIG. 3B. In both cases, the flexible element 5 is lodged into a microgroove 8, shown in FIGS. 4 and 5.

Figure 4:
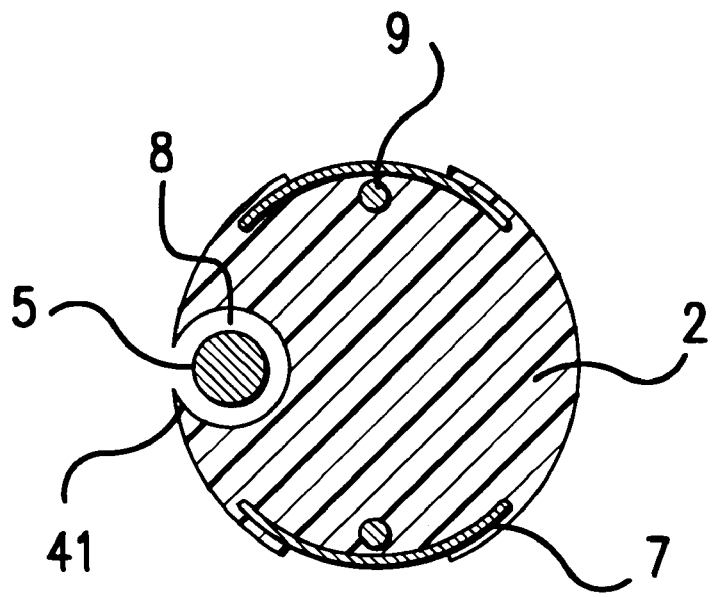
FIG. 4 is a cross section view of an electrode array with a wire in a circular microgroove which is tangent to the outer surface of the carrier.
Figure 5:
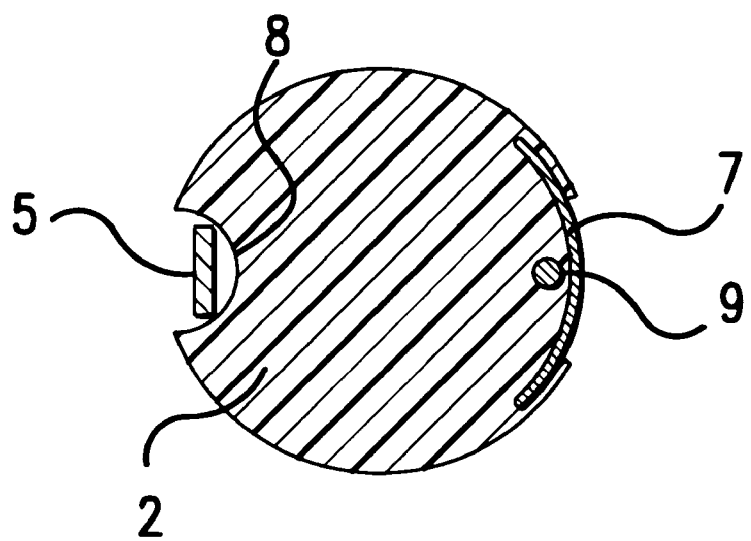
FIG. 5 is a cross section view of an electrode array with a ribbon in a u-shaped microgroove with a single electrode contact diametrically opposed to the microgroove.

FIG. 4 shows the electrode carrier 2 with a microgroove 8. The microgroove is designed to receive the flexible element 5. The cross section of the microgroove 8 may be circular, as shown on FIG. 4, unshaped, as shown on FIG. 5, or elliptical, rectangular, square, or any other shape which may be profitable. The cross sectional area of microgroove 8 may encompass up to 50% of that of the electrode carrier 2. The position of the microgroove 8 on the electrode carrier 2 may be flush or slightly recessed with respect to the outer surface of the electrode carrier 2. The combination of flush and recessed length affects the amount of force necessary during retro-positioning to dislodge the flexible element 5 embedded in the microgroove 8. It is desirable that the microgroove 8 be designed so that the embedded flexible element 5 dislodges easily out of the electrode carrier 2, while having enough constriction to maintain the flexible element 5 inside the microgroove 8 during insertion. The advantage of having a microgroove 8 in carrier 2 is that the overall electrode carrier presents a uniform and smooth surface to the tissue of the inner ear. Such a smooth surface has lower friction and facilitates insertion. Trauma is minimized and yet it is feasible to add elements into the groove to perform various desirable functions.

The negatively casted microgroove 8 is designed to receive a flexible element 5, a wire or a ribbon, for example. The flexible element 5 which is positioned in the microgroove 8 is preferably a 80 or 100 mm diameter super flexible nitinol wire with rounded edges, pieces of which may be produced by Nitinol Devices and Components Inc., Fremont, Calif., or EuroFlex, Pforzheim, Germany. The finished metal is preferably smoothed by electro polishing. The flexible element 5 can also be made in the form of a nitinol ribbon with rounded edges as shown on FIG. 5. In this case the microgroove 8 would likely be of rectangular or U shape in cross section. The flexible element 5 may also be a polymer rod, resistant to the heat necessary to fast cure the injection molded electrode carrier 2. The flexible element 5 can also be tapered in shape. In another embodiment, the flexible element 5 which is fitted in the microgroove 8 may be pre coated to impart biostability, biocompatibility, dielectric properties, hydrophobicity, and surface friction reduction properties. The surface coating may be done by Advance Surface technology Inc., Billerica Mass., or Specialty Coating Systems, Indianapolis. After the flexible element 5 and the electrode carrier 2 are fabricated, then the flexible element 5 is inserted into the tunnel 6, threaded through the microgroove 8, and lodged into the apical micro notch 11. In this manner the assembly of the 2 parts (flexible element 5 and electrode carrier 2) is most simple and economical.

The length of the microgroove 8 and flexible element 5 may be equal or shorter than the span of the inserted electrode carrier 2, as shown in FIGS. 3a and 3b. In the first case, apical section 22 is designed to lay against the outer wall and inner section 23 is designed to hug the inner wall 4 of the scala tympani 13. The advantage of a shorter microgroove 8 is that a full insertion of the electrode carrier 2 is facilitated. The apical section 22 of the electrode carrier 2 has no flexible element added to microgroove 8. In this case, four electrode contacts 7 may be variously distributed on apical section 22 of the electrode carrier 2. The remaining contacts 7, eight of them in FIG. 3A, may be closely or as widely spaced on inner section 23 of electrode carrier 2. The advantage of such a design is that it is possible for example, to stimulate 80% of the spiral ganglion cells 3 in Rosenthal's canal located near the basal turn of the cochlea, and also the residual proximal process, if any, which innervate the apex of the inner ear.

In an embodiment where the length of the microgroove 8 and flexible element 5 extend to the tip of electrode carrier 2, as shown in FIG. 3B, the insertion of the electrode carrier need not exceed 23 millimeters for the electrode carrier 2 to completely surround the Rosenthal's canal, following retro-positioning. Therewith, the electrode contacts 7 may be densely packed in the apical 12 to 15 millimeters of electrode carrier 2. It is calculated that up to 10 millimeters of electrode carrier 2 could be retracted after insertion. Retraction length however, depends on specific insertion depth and cochlea dimensions.

The preferred method of forming the microgroove 8 is by negative casting. The negative casting operation may be realized with an existing mold of uniform profile in which a nitinol wire of desired shape and diameter may be attached to one edge of the cast. The wire may be fastened to the mold with silicone. Following injection molding, the nitinol wire is easily removed by pulling it out of the molded carrier 2, effectively leaving a microgroove 8. If significantly recessed, the wire can be removed after cutting a slit with a micro scalpel above or near the location of the wire. The lips 41 of the microgroove 8 may be enlarged with micro-scissors. Monolithic molds may also be designed to include the formation of the microgroove 8.

Figure 6:
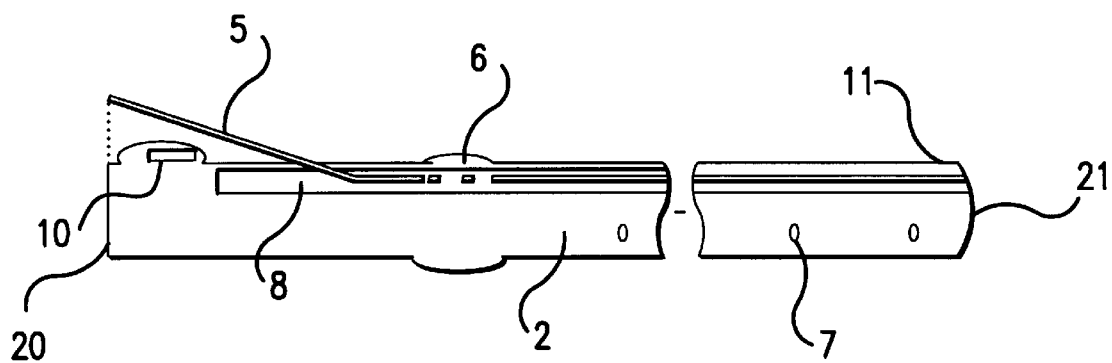
FIG. 6 is a longitudinal view of an electrode array showing the microgroove, tunnel, apical and basal silicon micro notches, and a wire-like element in the microgroove.

Referring to FIG. 6, the most apical end 21 of the microgroove 8 is terminated in the form of a micro notch 11 a few millimeters long. The micro notch 11 is designed to loosely or tightly hold the apical end of the flexible element 5. At the basal end 20 of the electrode carrier 2, just posterior to the full insertion length of the electrode carrier (typically 30 millimeters or less), a short silicone bridge a few millimeters long covers the microgroove 8 forming a tunnel 6 through which the flexible member passes. Microgroove 8 extends past the bridge 6 in basal direction 20, for some distance.

At points posterior to the short tunnel 6, are located several notches 10 which are, for example, 5 millimeters apart. The notches 10 may be 2 millimeters deep by way of illustration. The notches 10 are designed to receive the basal end 20 of the flexible element 5 located into the microgroove 8, and to provide a locking mechanism for the flexible element 5, following retro-positioning of the electrode carrier 2. The cross sectional shape and inner dimensions of the notches 10 are therefore made similar to that of the flexible element 5. Such notches 10 as described here are easily and economically built by covering small separate segments of flexible element 5 with silicone. The subsequent curing process causes excellent bonding between the silicone of notch 10 and that of carrier 2 (silicone to silicone bonding). Removal of the small separate segments of flexible element 5 leaves perfect notches 10. The cross sectional dimensions of notch 10 can also be made larger than those of flexible element 5 to facilitate the introduction of the most basal end 20 of the flexible element 5 into the notch 10.

Figure 7A:
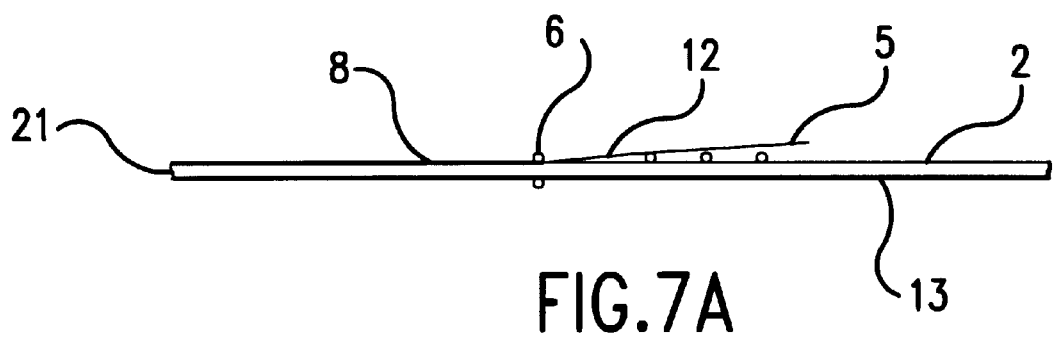
FIGS. 7A and 7B are respective views of the basal portion of an electrode array before and after the retro positioning technique.
Figure 7B:
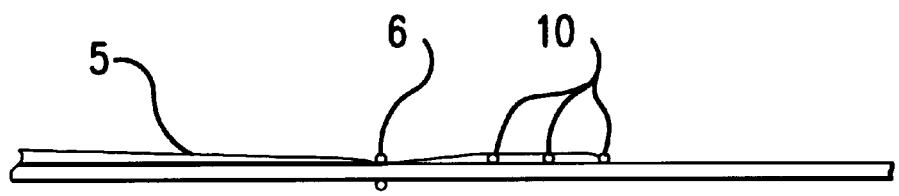

Referring now to FIG. 7A, after the full or partial insertion of the electrode array 2 into the scala tympani, the surgeon hold the flexible element 5 with some tools such as micro forceps at location 12 of apical end 20. The surgeon then retract the electrode carrier 2, held at location 13, for example, with the other hand. The electrode carrier 2 retracts easily until it is wrapped around inner scala tympani wall 4. At this point, the surgeon inserts the basal end 20 of flexible element 5 into one of the notches 10, as depicted in FIG. 7B. A cross sectional view of the final position of electrode carrier 2 and flexible element 5 is shown in FIG. 2B.

Figure 8A:
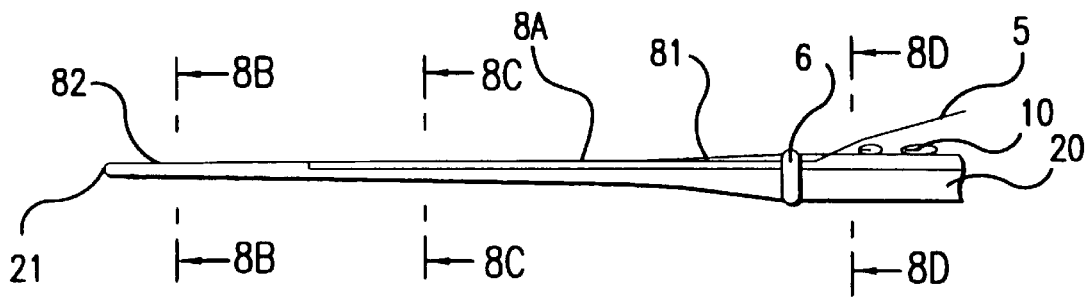
FIG. 8A illustrates a side view of a partitioned electrode array before insertion.
Figure 8B:
FIGS. 8B, 8C, and 8D are cross sectional views of the array of FIG. 8A.
Figure 8C:
Figure 8D:
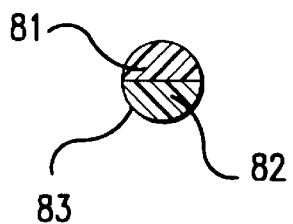
Figure 8E:
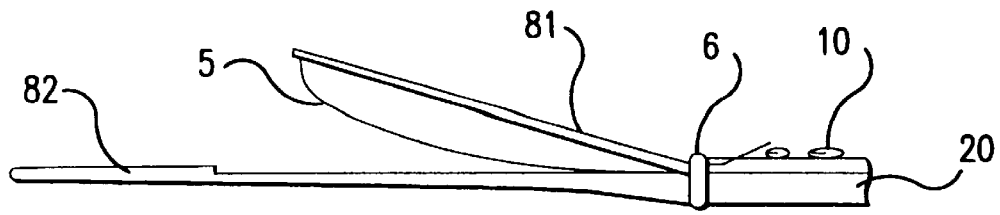
FIG. 8E is a side view of the array of FIG. 8A after insertion with the perimodiolar segment lifted.

Another embodiment of the present invention is directed to a partitioned perimodiolar electrode carrier. Such an electrode carrier is shown in FIG. 8A. FIG. 8A–D illustrate a cross sections of the electrode carrier at three representative locations. The intra-cochlear electrode carrier is segmented into a perimodiolar section 81 and an outer wall facing branch 82. The portion of the electrode carrier situated posterior to the entrance of the cochlea is in the form of a monolithic silicone matrix 83. Thus, perimodiolar section 81 and outer wall facing branch 82 are silicone bonded together to form monolithic silicone matrix 83.

In a preferred embodiment, the segments 81 and 82 are of unequal length (1 to 2 ratio for example). The perimodiolar segment 81 is shorter than the outer wall facing segment 82 to accommodate the real length difference between the inner and outer wall 1 and 3 of the scala tympani 13. Initially, and during insertion of the carrier, the two segments 81 and 82 are aligned and held together, for instance with a pre-molded microgroove 92 into which fits a pre-molded micro protuberance 91 as show in FIGS. 9A and 9B. It is understood that the pre-molded parts may be of any shape, form, length, and situated at any location on segments 81 and 82. Such pre-molded shapes are easily and economically built by negative casting as described earlier.

Figure 9A:
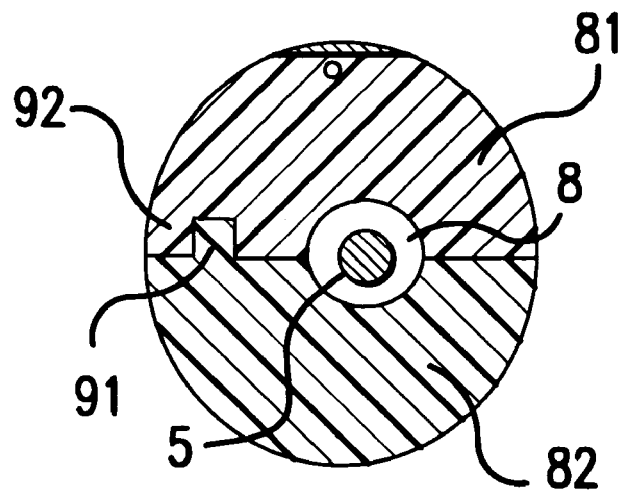
FIGS. 9A and 9B are cross section views of partitioned electrode arrays having two different methods of attachment and alignment of the branches.
Figure 9B:
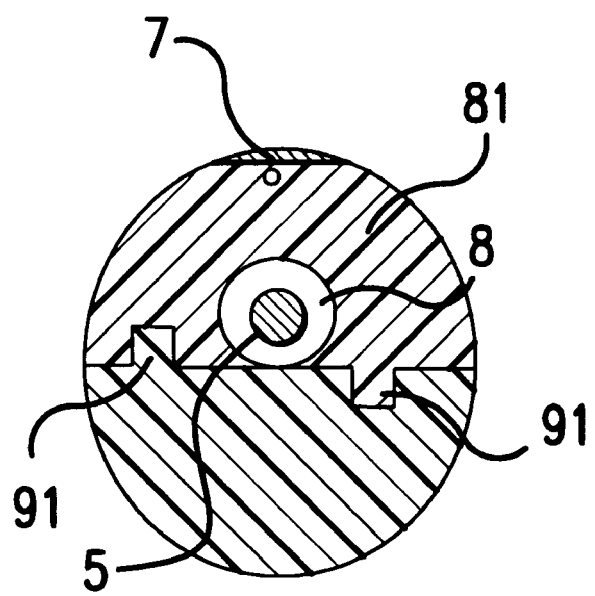

Shortly after full insertion of the whole carrier, the perimodiolar section 81 is separated from the outer wall facing segment 82. The perimodiolar section 81 is then launched toward the inner wall 4 of the scala tympani 13 with the help of flexible element 5 which is located between the two segments 81 and 82 in microgroove 8. Microgroove 8 may be divided between segments 81 and 82, as shown in FIG. 9A, or it may be flush with one segment, 81 for example, as shown on FIG. 9B. Any other combination of flush, recessed, centered and eccentric locations for microgroove 8 may also be used as deemed profitable to the design.

The flexible element 5 lodged between the two segments 81 and 82 is again super-flexible nitinol wire. It may also be any polymeric rod flexible and strong enough to arch the perimodiolar section 81 and compel the perimodiolar section 81 to conform to the inner contour 4 of the scala tympani. The preferred method for actively displacing the perimodiolar segment 81 is by retro-positioning of the electrode carrier as described previously. An alternative embodiment method for actively displacing the perimodiolar segment 81 is by exerting a forward force on the flexible element 5 in microgroove. The force exerted in the direction of the long axis of the electrode carrier dislodges flexible element 5 from the microgroove 8. At the same time the perimodiolar segment 81 is moved in a forward and radial direction toward the inner wall 4 of the scala tympani 13. The microgroove 8 may be constructed as described previously, and it may be located on either one or both branches 81 and 82 of the electrode carrier. The spatial distribution of the electrodes 7 on the segmented carrier may be as deemed profitable. In one preferred embodiment, four electrodes each 2.4 millimeters apart are situated on the apical part 21 of the outer wall facing branch 82, and eight contacts each 1.1 millimeters apart are distributed on the apical section of the perimodiolar branch 81.

The advantage of such a segmented electrode design is that one branch of the electrode carrier is fully, or maximally inserted, while another branch surrounds the inner scala tympani wall. With electrode contacts variously distributed on the two segments of the electrode carrier, it is feasible to stimulate both spiral ganglion cells, 80% of which are located near the cochlear basal turn, and existing residual neural tissue in the upper turns of the cochlea.

In yet another embodiment of the invention the electrode carrier is again a segmented two branch design as shown in FIGS. 8A–E. The perimodiolar branch 81, however, is pre-shaped to the form of the inner wall 4 of the scala tympani 13. The memory shaped form of the perimodiolar branch 81 is held straight by mean of a nitinol rod flexible element 5 which fits between the pre-shaped perimodiolar branch 81 and the outer wall facing branch 82. At the apical end of the carrier, a notch, 11 as in FIG. 6, receives the apical end of the nitinol rod flexible element 5. The flexible element 5 slides freely in the micro notch 11. After full insertion of the electrode carrier composed of perimodiolar section 81 and outer wall facing section 82 in the scala tympani 13, the nitinol rod flexible element 5 is pulled back slightly out of the notch 11. The released perimodiolar branch 81 then assumes its pre-shaped form.

Figure 10:
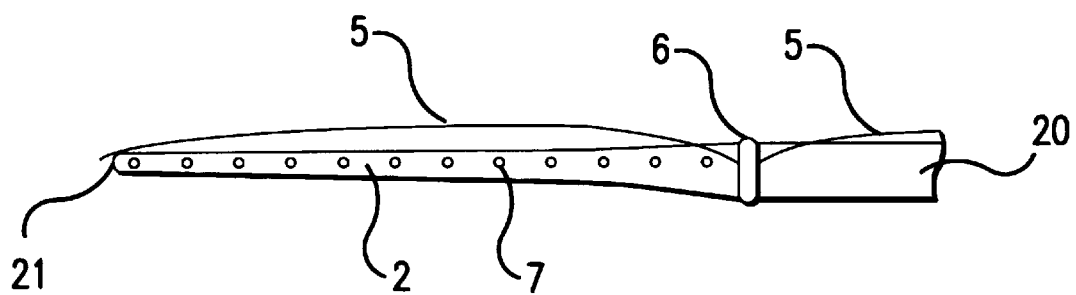
FIG. 10 illustrates an electrode array with an external rod for retro positioning.

In yet another embodiment, the flexible element 5 is placed outside and parallel to the electrode carrier 2 instead of in a microgroove. This is shown in FIG. 10. While the electrode carrier has no molded microgroove 8, the electrode carrier again has a micro notch at the apex 21 (not shown), a tunnel 6 at the basal end 20, and several basal notches (not shown) posterior to the basal end 20. The flexible element 5 is again made of a super-flexible nitinol wire 100 mm in diameter, for example, and is threaded through the basal tunnel 6 and into the apical micro notch not shown. Insertion of the electrode carrier 2 with the flexible element 5 is done by alternatingly pushing the electrode carrier 2 and the flexible element 5 into the scala tympani 13. After full or partial insertion the carrier 2 is retro-positioned as it has been described earlier.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. An implantable cochlear electrode array comprising:
    an electrode carrier having a outer end and an inner end, to electrically stimulate a scala tympani wall of a cochlea in which the carrier is implanted;
    a groove within the electrode carrier extending from the outer end of the electrode carrier at least part way towards the inner end; and
    a flexible element located in the groove and attached to the electrode carrier towards the inner end;
    wherein the carrier and the flexible element are arranged with respect to each other so that, after the electrode array is inserted in a cochlea, movement of the carrier with respect to the flexible element, towards the outer end, causes at least a portion of the electrode carrier to wrap around an inner scala tympani wall.

2. A cochlear electrode array as in claim 1, wherein the groove has a fixed cross-sectional shape.

3. A cochlear electrode array as in claim 2, wherein the cross-sectional shape of the groove is circular.

4. A cochlear electrode array as in claim 2, wherein the cross-sectional shape of the groove is rectangular.

5. A cochlear electrode array as in claim 2, wherein the cross-sectional shape of the groove is u-shaped.

6. A cochlear electrode array as in claim 1, wherein the groove has a variable cross-sectional shape.

7. A cochlear electrode array as in claim 1, wherein the groove is substantially parallel to a long axis of the electrode carrier.

8. A cochlear electrode array as in claim 1, wherein the groove significantly deviates from a long axis of the electrode carrier.

9. A cochlear electrode array as in claim 1, wherein the groove has an inner notch located near the inner end to maintain the inner end of the flexible member and an adjacent portion of the electrode carrier together.

10. A cochlear electrode array as in claim 1, wherein the flexible element is a wire made of biocompatible material.

11. A cochlear electrode array as in claim 10, wherein the wire is made of nitinol.

12. A cochlear electrode array as in claim 10, wherein the wire has a surface coating to modify its surface characteristics.

13. A cochlear electrode array as in claim 10, wherein the wire has a surface coating to modify its dielectric characteristics.

14. A cochlear electrode array as in claim 1, wherein the flexible element is a flexible polymeric rod.

15. A cochlear electrode array as in claim 1, wherein a portion of the inner end of the electrode carrier extends beyond the inner ends of the groove and the flexible element so that the inner end of the electrode carrier does not wrap around the inner scala tympani wall when the electrode carrier is partially withdrawn after insertion in the cochlea.

16. A cochlear electrode array as in claim 1, further including:
    a bridge portion of the electrode carrier located near the outer end of the electrode carrier which closes over the surface penetration of the groove to form a closed tunnel around the flexible element and to prevent the flexible element from lifting out of the groove at the bridge.

17. A cochlear electrode array as in claim 1, further including:
    at least one outer notch near the outer end of the electrode carrier to securely hold the outer end of the flexible member after the electrode array has been implanted in the cochlea.

18. A cochlear electrode array as in claim 1, wherein the carrier and the flexible element are further arranged with respect to each other so that, after the electrode array is inserted in a cochlea, movement of the carrier with respect to the flexible element, towards the outer end, pulls the electrode carrier away from the flexible element, which emerges from the groove through the surface of the electrode carrier, except where the electrode carrier and the flexible element are attached, so that the electrode carrier wraps around an inner scala tympani wall.

19. An implantable cochlear electrode array comprising:
   an electrode carrier having a outer end and an inner end, to electrically stimulate a scala tympani wall of a cochlea in which the carrier is implanted, wherein the electrode carrier further comprises:
      a perimodiolar section to be positioned next to an inner scala tympani wall of the cochlea, and
      an outer wall section to be positioned next to an outer scala tympani wall of the cochlea;
   a groove within the electrode carrier extending from the outer end of the electrode carrier at least part way towards the inner end wherein at least a portion of the groove penetrates the surface of the electrode carrier; and
   a flexible element located in the groove and attached to the electrode carrier towards the inner end;
   wherein the carrier and the flexible element are arranged with respect to each other so that, after the electrode array is inserted in a cochlea, movement of the carrier with respect to the flexible element, towards the outer end, causes the perimodiolar section of the electrode carrier to wrap around an inner scala tympani wall.

20. A cochlear electrode array as in claim 19, wherein the groove has a fixed cross-sectional shape.

21. A cochlear electrode array as in claim 20, wherein the cross-sectional shape of the groove is circular.

22. A cochlear electrode array as in claim 20, wherein the cross-sectional shape of the groove is rectangular.

23. A cochlear electrode array as in claim 20, wherein the cross-sectional shape of the groove is u-shaped.

24. A cochlear electrode array as in claim 19, wherein the groove has a variable cross-sectional shape.

25. A cochlear electrode array as in claim 19, wherein the groove is substantially parallel to a long axis of the electrode carrier.

26. A cochlear electrode array as in claim 19, wherein the groove significantly deviates from a long axis of the electrode carrier.

27. A cochlear electrode array as in claim 19, wherein the groove has an inner notch located near the inner end to maintain the inner end of the flexible member and an adjacent portion of the electrode carrier together.

28. A cochlear electrode array as in claim 19, wherein the groove is within the perimodiolar section of the electrode carrier.

29. A cochlear electrode array as in claim 19, wherein the groove is within the outer wall section of the electrode carrier.

30. A cochlear electrode array as in claim 19, wherein the flexible element is a wire made of biocompatible material.

31. A cochlear electrode array as in claim 30, wherein the wire is made of nitinol.

32. A cochlear electrode array as in claim 30, wherein the wire has a surface coating to modify its surface characteristics.

33. A cochlear electrode array as in claim 30, wherein the wire has a surface coating to modify its dielectric characteristics.

34. A cochlear electrode array as in claim 19, wherein the flexible element is a flexible polymeric rod.

35. A cochlear electrode array as in claim 19, further including:
   a bridge portion of the electrode carrier located near the outer end of the electrode carrier which closes over the surface penetration of the groove to form a closed tunnel around the flexible element and to prevent the flexible element from lifting out of the groove at the bridge.

36. A cochlear electrode array as in claim 19, further including:
   at least one outer notch near the outer end of the electrode carrier to securely hold the outer end of the flexible member after the electrode array has been implanted in the cochlea.

37. A cochlear electrode array as in claim 19, wherein the perimodiolar section is shorter than the outer wall section to accommodate the real length difference between the inner and outer walls of the scala tympani of a cochlea.

38. A cochlear electrode array as in claim 19, wherein the carrier and the flexible element are further arranged with respect to each other so that, after the electrode array is inserted in a cochlea, movement of the carrier with respect to the flexible element, towards the outer end, pulls the perimodiolar section of the electrode carrier away from the flexible element, which emerges from the groove through the surface of the electrode carrier, except where the electrode carrier and the flexible element are attached, so that the perimodiolar section of the electrode carrier wraps around an inner scala tympani wall.

* * * * *